US010525062B2

(12) United States Patent
Theisinger et al.

(10) Patent No.: US 10,525,062 B2
(45) Date of Patent: Jan. 7, 2020

(54) PHARMACEUTICAL COMPOSITION FOR TREATMENT OF INCREASED INTRAOCULAR PRESSURE

(71) Applicants: Bastian Theisinger, Mannheim (DE); Sonja Theisinger, Mannheim (DE); Bernhard Günther, Dossenheim (DE)

(72) Inventors: Bastian Theisinger, Mannheim (DE); Sonja Theisinger, Mannheim (DE); Bernhard Günther, Dossenheim (DE)

(73) Assignee: NOVALIQ GMBH, Heidelberg (DE)

( * ) Notice: Subject to any disclaimer, the term of this patent is extended or adjusted under 35 U.S.C. 154(b) by 0 days.

(21) Appl. No.: 16/017,805

(22) Filed: Jun. 25, 2018

(65) Prior Publication Data

US 2018/0303849 A1    Oct. 25, 2018

Related U.S. Application Data

(62) Division of application No. 13/581,396, filed as application No. PCT/EP2011/053949 on Mar. 16, 2011, now Pat. No. 10,045,996.

(30) Foreign Application Priority Data

Mar. 17, 2010 (EP) .................................. 10002800

(51) Int. Cl.
*A61K 31/5575* (2006.01)
*A61K 9/00* (2006.01)
*A61K 9/08* (2006.01)
*A61K 47/06* (2006.01)

(52) U.S. Cl.
CPC ........ *A61K 31/5575* (2013.01); *A61K 9/0048* (2013.01); *A61K 9/08* (2013.01); *A61K 47/06* (2013.01)

(58) Field of Classification Search
None
See application file for complete search history.

(56) References Cited

U.S. PATENT DOCUMENTS

| | | |
|---|---|---|
| 2,616,927 A | 11/1952 | Kauck et al. |
| 5,077,036 A | 12/1991 | Long, Jr. |
| 5,326,566 A | 7/1994 | Parab |
| 5,336,175 A | 8/1994 | Mames |
| 5,518,731 A | 5/1996 | Meadows |
| 5,667,809 A | 9/1997 | Trevino |
| 5,874,469 A | 2/1999 | Maniar et al. |
| 5,874,481 A | 2/1999 | Weers |
| 5,981,607 A | 11/1999 | Ding |
| 6,042,845 A | 3/2000 | Sun et al. |
| 6,113,919 A | 9/2000 | Cronelus |
| 6,159,977 A | 12/2000 | Reeves |
| 6,177,477 B1 | 1/2001 | George et al. |
| 6,197,323 B1 | 3/2001 | Georgieff |
| 6,224,887 B1 | 5/2001 | Samour et al. |
| 6,262,126 B1 | 7/2001 | Meinert |
| 6,372,243 B2 | 4/2002 | Kobuch et al. |
| 6,391,879 B1 | 5/2002 | Reeves |
| 6,458,376 B1 | 10/2002 | Meadows |
| 6,486,212 B2 | 11/2002 | Meinert |
| 6,489,367 B1 | 12/2002 | Meinert |
| 6,730,328 B2 | 5/2004 | Maskiewicz |
| 7,001,607 B1 | 2/2006 | Menz |
| 7,026,359 B1 | 4/2006 | Gross |
| 7,258,869 B1 | 8/2007 | Berry |
| 7,740,875 B2 | 6/2010 | Dechow |
| 8,029,977 B2 | 10/2011 | Meinert et al. |
| 8,470,873 B2 | 6/2013 | Chen |
| 8,614,178 B2 | 12/2013 | Theisinger et al. |
| 8,796,340 B2 | 8/2014 | Theisinger et al. |
| 8,916,157 B2 | 12/2014 | Krause et al. |
| 8,986,738 B2 | 3/2015 | Meinert |
| 9,241,900 B2 | 1/2016 | Wilson |
| 9,308,262 B2 | 4/2016 | Günther et al. |
| 10,045,996 B2 | 8/2018 | Theisinger et al. |
| 2002/0128527 A1 | 9/2002 | Meinert |
| 2003/0018044 A1 | 1/2003 | Peyman |
| 2003/0027833 A1 | 2/2003 | Cleary et al. |
| 2004/0044045 A1 | 3/2004 | Burk |
| 2004/0082660 A1 | 4/2004 | Ueno |
| 2004/0265362 A1 | 12/2004 | Susilo |
| 2004/0266702 A1 | 12/2004 | Dawson |

(Continued)

FOREIGN PATENT DOCUMENTS

| | | |
|---|---|---|
| EP | 0 089 815 | 9/1983 |
| EP | 0 670 159 | 9/1995 |

(Continued)

OTHER PUBLICATIONS

Ahmed, et al., "Disposition of Timolol and Inulin in the Rabbit Eye Following Corneal Versus Non-Corneal Absorption," International Journal of Pharmaceutics, 1987, 38:9-21.
Baerdemaeker, "Pharmacokinetics in Obese Patients," Continuing Education in Anesthesia, Critical Care & Pain, 2004, 4:152-155.
Blackie et al., "MGD: Getting to the Root Cause of Dry Eye", Review of Optometry, 2012, pp. 1-12.
Broniatowski, M. et al., "Langmuir Monolayers Characteristics of Perfluorodecyl)-Alkanes," Journal of Physical Chemistry B, 2004, 108:13403-13411.
Chemical Book, "5-Fluorouracil," available at http://www.chemicalbook.com/-ChemicalProductProperty_EN_CB8162744.htm>, accessed Mar. 7, 2014.

(Continued)

*Primary Examiner* — Jeffrey S Lundgren
*Assistant Examiner* — Stephanie K Springer
(74) *Attorney, Agent, or Firm* — Hoxie & Associates LLC

(57) ABSTRACT

The invention provides novel pharmaceutical compositions for the treatment of increased intraocular pressure based on semifluorinated alkanes which are useful as carriers for a broad range of active ingredients. Preferred active ingredients include poorly water-soluble prostaglandin analogues. The compositions can be administered topically into the eye. The invention further provides kits comprising such compositions.

10 Claims, No Drawings

(56) References Cited

U.S. PATENT DOCUMENTS

| | | |
|---|---|---|
| 2005/0079210 A1 | 4/2005 | Gupta |
| 2005/0175541 A1 | 8/2005 | Lanza et al. |
| 2008/0207537 A1 | 8/2008 | Turner et al. |
| 2008/0260656 A1 | 10/2008 | Mallard |
| 2009/0149546 A1 | 6/2009 | Chang |
| 2009/0226875 A1 | 9/2009 | Meinert |
| 2010/0008996 A1 | 1/2010 | Meinert |
| 2010/0226997 A1 | 9/2010 | Bowman et al. |
| 2010/0274215 A1 | 10/2010 | Wong et al. |
| 2011/0269704 A1 | 11/2011 | Seigfried |
| 2012/0010280 A1 | 1/2012 | Aleo et al. |
| 2012/0095097 A1 | 4/2012 | Tabuchi et al. |
| 2012/0238639 A1 | 9/2012 | Theisinger et al. |
| 2013/0046014 A1 | 2/2013 | Theisinger et al. |
| 2013/0266652 A1 | 10/2013 | Theisinger et al. |
| 2013/0303473 A1 | 11/2013 | Wilson |
| 2014/0004197 A1 | 1/2014 | Theisinger et al. |
| 2014/0100180 A1 | 4/2014 | Günther et al. |
| 2014/0140942 A1 | 5/2014 | Günther et al. |
| 2014/0369993 A1 | 12/2014 | Günther et al. |
| 2015/0224064 A1 | 8/2015 | Günther et al. |
| 2015/0238605 A1 | 8/2015 | Günther et al. |
| 2016/0101178 A1 | 4/2016 | Wilson |
| 2016/0159902 A1 | 6/2016 | Günther et al. |
| 2017/0087100 A1 | 3/2017 | Scherer et al. |
| 2017/0087101 A1 | 3/2017 | Scherer et al. |
| 2017/0182060 A1 | 6/2017 | Wiedersberg et al. |

FOREIGN PATENT DOCUMENTS

| | | |
|---|---|---|
| EP | 0 965 329 | 12/1999 |
| EP | 0 965 334 | 12/1999 |
| EP | 1 152 749 | 11/2001 |
| EP | 0 939 655 | 6/2002 |
| EP | 2 110 126 | 10/2009 |
| EP | 2 332 525 | 6/2011 |
| EP | 2 335 735 | 6/2011 |
| EP | 2 462 921 | 6/2012 |
| JP | S6452722 | 2/1989 |
| JP | 2000511157 | 8/2000 |
| WO | WO 96/40052 | 12/1996 |
| WO | WO 2000/024376 | 5/2000 |
| WO | WO 2000/054588 | 9/2000 |
| WO | WO 02/49631 | 6/2002 |
| WO | WO 2005/099718 | 10/2005 |
| WO | WO 2005/099752 | 10/2005 |
| WO | WO 2005/123035 | 12/2005 |
| WO | WO 2006/007510 | 1/2006 |
| WO | WO 2006/042059 | 4/2006 |
| WO | WO 2006/048242 | 5/2006 |
| WO | WO 2007/052288 | 5/2007 |
| WO | WO 2008/060359 | 5/2008 |
| WO | WO 2009/013435 | 1/2009 |
| WO | WO 2009/065565 | 5/2009 |
| WO | WO 2010/062394 | 6/2010 |
| WO | WO 2010/146536 | 12/2010 |
| WO | WO 2011/009436 | 1/2011 |
| WO | WO 2011/073134 | 6/2011 |
| WO | WO 2011/113855 | 9/2011 |
| WO | WO 2012/052418 | 4/2012 |
| WO | WO 2012/062834 | 5/2012 |
| WO | WO 2012/093113 | 7/2012 |
| WO | WO 2012/121754 | 9/2012 |
| WO | WO 2012/160179 | 11/2012 |
| WO | WO 2012/160180 | 11/2012 |
| WO | WO 2013/110621 | 8/2013 |
| WO | WO 2014/041055 | 3/2014 |
| WO | WO 2014/041071 | 3/2014 |
| WO | WO 2015/011199 | 1/2015 |

OTHER PUBLICATIONS

Davies, "Biopharmaceutical Considerations in Topical Ocular Drug Delivery," Clin. Exper. Pharmacol. Physiol., 2000, 27:558-562.

Dembinski et al., Semi-fluorinated Alkanes as Carriers for Drug Targeting in Acute Respiratory Failure, Experimental Lung Research, 2010, 36(8):499-507.

Elkeeb et al., "Transungual Drug Delivery: Current Status," Int J Pharmaceutics, 2010, 384 (1-2):1-8.

English-language machine translation of EP0670159 (A1) issued in U.S. Appl. No. 14/122,025 on Apr. 1, 2015, 10 pages.

Freiburger Dokumentenserver (FreiDok), Albert-Ludwigs, Unversitat Feiburg im Breisgau, retrieved from the Internet, date accessed: Feb. 5, 2014, 2 pages URL: <http://www.freidok.uni-freiburg.de/volltexte/5682>.

Gayton, J., "Etiology, Prevalence, and Treatment of Dry Eye Disease," Clinical Ophthalmology, 2009, 3:405-412.

Gerdenitsch, "Emulsions—established and promising drug carriers for parenteral administration", retrieved from Internet, date accessed: Jun. 20, 2016, URL: <http:ipimediaworld.com/wp-content/uploads/2012/05/Pages-from-IPI-Volume-2-Issue-1-11.pdf.>.

Griffin, W., "Classification of Surface-Active Agents by 'HLB'," Journal of the Society of Cosmetic Chemists, 1949, 1:311-326.

Hardung, H., "Semifluorierte und perfluorierte Vergindungen zur topischen und parenteralen Anwendung," 2008, retrieved from Internet, date accessed: Oct. 10, 2011, URL: <http://www.freidok.uni-freiburg.de/volltexte/5682/pdf/Dissertation_Hardung.pdf>.

Hoerauf et al., "Combined Use of Partially Fluorinated Alkanes, Perfluorocarbon Liquids and Silicone Oil: An Experimental Study," Graefe's Archive for Clinical and Experimental Ophthalmology, 2001, 239(5):373-381.

International Preliminary Report on Patentability dated Apr. 23, 2013, for International Patent Application PCT/EP2011/068141, 4 Pages.

International Preliminary Report on Patentability dated May 14, 2013, for International Patent Application PCT/EP2011/069795, 8 Pages.

International Preliminary Report on Patentability dated Jul. 10, 2013, for International Patent Application PCT/EP2012/050043, 5 Pages.

International Preliminary Report on Patentability dated Nov. 26, 2013, for International Patent Application PCT/EP2012/059787, 9 Pages.

International Preliminary Report on Patentability dated Nov. 26, 2013, for International Patent Application PCT/EP2012/059788, 8 Pages.

International Preliminary Report on Patentability dated Jul. 29, 2014, for International Application No. PCT/EP2013/051163, 7 pages.

International Preliminary Report on Patentability dated Mar. 17, 2015, for International Application No. PCT/EP2013/068882, 5 pages.

International Preliminary Report on Patentability dated Mar. 17, 2015, for International Application No. PCT/EP2013/068909, 7 pages.

International Preliminary Report on Patentability dated Jan. 26, 2016, for International Application No. PCT/EP2014/065840, 11 pages.

International Search Report for International Application No. PCT/EP2011/068141 dated Dec. 14, 2011, 2 pages.

International Search Report for International Patent Application PCT/EP2011/069795 dated Jan. 16, 2012, 3 pages.

International Search Report for International Patent Application PCT/EP2012/050043 dated Apr. 24, 2012, 2 pages.

International Search Report for International Application No. PCT/EP2012/059787 dated Dec. 5, 2012, 4 pages.

International Search Report for International Application No. PCT/EP2012/059788 dated Dec. 3, 2012, 4 pages.

International Search Report for International Application No. PCT/EP2013/051163 dated Mar. 4, 2013, 4 pages.

International Search Report for International Application No. PCT/EP2013/068882 dated Oct. 30, 2013, 4 pages.

International Search Report for International Application No. PCT/EP2013/068909 dated Dec. 5, 2013, 4 pages.

International Search Report for International Application No. PCT/EP2014/065840 dated Oct. 7, 2014, 3 pages.

JP 2000511157A, English Machine Translation of the Abstract, Description, and Claims, Espacenet, Date Accessed: Feb. 10, 2016.

(56) References Cited

OTHER PUBLICATIONS

JPS6452722, English Machine Translation of the Abstract, Description, and Claims, Espacenet, Date Accessed: Feb. 10, 2016.
Kaercher et al., "NovaTears® as new Therapy in Dry Eye Results from three prospective, multicenter, non-interventional studies in different patient populations", TFOS Conference (Tear Film & Ocular Surface), Sep. 7-10, 2016, Montpellier, France, Poster Session II, Poster No. 60, 1 page.
Knepp, "Stability of Nonaqueous Suspension Formulations of Plasma Derived Factor IX and Recombinant Human Alpha Interferon at Elevated Temperatures," Pharmaceutical Research, 1998, 15(7):1090-1095.
Kociok, N., "Influence on Membrane-Mediated Cell Activation by Vesicles of Silicone Oil or Perfluorohexyloctane," Graefe's Archive for Clinical and Experimental Ophthalmology, 2005, 243, 345-358.
Lemp, M., Management of Dry Eye Disease, The American Journal of Managed Care, 2008, 14(3):S88-S101.
Mackiewicz, J. et al., "In Vivo Retinal Tolerance of Various Heavy Silicone Oils," Investigative Ophthalmology & Visual Science, 2007, 48(4):1873-1883.
Meinert et al., "Semifluorinated alkanes—A new class of compounds with outstanding properties for use in ophthalmology," European Journal of Ophthalmology, 2000, 10 (3):189-197.
Meinert et al., Biomaterials, Artificial Cells, and Immobilization Biotechnology, 1993, 21(5):583-95.
Messmer et al., "Semifluorierte Alkane als Therapie bei Meibomdrüsen-Dysfunktion Ergebnisse einer prospektiven, multizentrischen Beobachtungsstudie", Presentation, DOG-Kongress, Sep. 29-Oct. 2, 2016, Berlin DOG (Deutsche Ophtalmologische Gesellschaft), Poster No. PSa03-02, 1 page (German langrage version).
Messmer et al., "Semifluorinated Alkanes as a Therapy for Meibomian Gland Dysfunction Results of a prospective, multi-centered observational study", Presentation, DOG-Kongress, Sep. 29, 2016-Oct. 2, 2016, Berlin DOG (Deutsche Ophtalmologische Gesellschaft), Poster No. PSa03-02, English Translation, 6 pages.
Messmer et al. "Semifluorinated Alkanes as a Therapy for Meibomian Gland Dysfunction Results of a prospective, multi-centered observational study", Presentation, DOG-Kongress, Sep. 29, 2016-Oct. 2, 2016, Berlin DOG (Deutsche Ophtalmologische Gesellschaft), Ophthalmologe, Aug. 2016 Poster No. PSa03-02, English Translation of Abstract, p. 138.
Murdan et al., "Enhancing the Nail Permeability of Topically Applied Drugs," Exp Opin Drug Delivery, 2008, 5(11):1267-1282.
Perry, "Dry Eye Disease: Pathophysiology, Classification, and Diagnosis," The American Journal of Managed Care, 2008, 14(3):S79-S87.
Pinarci et al., "Intraocular Gas Application in the Diagnosis and Treatment of Valsalva Retiopathy in Case with Premacular Hemorrhage," Retina-Vitreus, 2009, 17(2):153-155 (Abstract Only).
Plassmann, M. et al., "Trace Analytical Methods for Semifluorinated n-Alkanes in Snow, Soil, and Air," Analytical Chemistry, 2010, 82(11):4551-4557.
Plassmann, M. et al., "Theoretical and Experimental Simulation of the Fate of Semifluorinated n-Alkanes During Snowmelt," Environmental Science & Technology, 2010, 44(17):6692-6697.
Rosca-Casian et al., "Antifungal Activity of Aloe Vera Leaves," Fitoterapia, 2007, 78(3):219-222.
Rosenberg, A.S., "Effect of Protein Aggregates: An Immunologic Perspective," The AAPS Journal, 2006, 8(3):E501-E507.
Stevenson, "Characterization of Protein and Peptide Stability and Solubility in Non-Aqueous Solvents," Current Pharmaceutical Biotechnology, 2000, 1:165-182.
Troiano et al., "Effect of Hypotonic .4% Hyaluronic Acid Drops in Dry Eye Patients: A Cross-Study", Cornea 27(10): 1126-1130 (Abstract Only).
Wang, W., "Lyophilization and Development of Solid Protein Pharmaceuticals," Int. J. Pharm., 2000, 203:1-60.
Wong et al., "Perfluorocarbons and Semifluorinated Alkanes," Seminars in Ophthalmology; vol. 15 (1), 2000, p. 25-35.
Xalatan, Latanoprost Ophthalmic Solution, 50 μg/mL Prostaglandin $F_{2\alpha}$ analogue, Product Monograph, Jul. 21, 2014, 30 pages.
Chhadva et al., "Meibomian Gland Disease The Role of Gland Dysfunction in Drye Eye Disease," Ophthalmology (2017) 124(11 Supplement): S20-S26.
Gehlsen et al., "A semifluorinated alkane (F4H5) as novel carrier for cyclosporine A: a promising therapeutic and prophylactic option for topical treatment of dry eye," Graefe's Arch. Clin. Exp. Ophthalmol., (2017) 255(4):767-775.
Messmer, E.M., "The Pathophysiology, Diagnosis, and Treatment of Dry Eye Disease," (2015) Deutsches Arzteblatt International, 112(5):71-82.
Pflugfelder et al., "The Pathophysiology of Dry Eye Disease What We Know and Future Directions for Research," Ophthalmology (2017) 124(11 Supplement): S4-S13.
Steven, P. et al. "Semifluorinated Alkane Eye Drops for Treatment of Dry Eye Disease—A Prospective, Multicenter Noninterventional Study," Journal of Ocular Pharmacology and Therapeutics (2015) 31(8):498-503.
Steven et al., "Semifluorinated Alkane Eye Drops for Treatment of Dry Eye Disease Due to Meibomian Gland Disease," Journal of Ocular Pharmacology and Therapeutics (2017) 33(9):1-8.

PHARMACEUTICAL COMPOSITION FOR TREATMENT OF INCREASED INTRAOCULAR PRESSURE

CROSS REFERENCE TO RELATED APPLICATIONS

This application is a division of U.S. application Ser. No. 13/581,396, filed on Aug. 27, 2012, which is a National Stage Application filed under 35 U.S.C. § 371 of International Application No. PCT/EP2011/053949 filed on Mar. 16, 2011, which claims benefit to and priority of European Patent Application No. 10002800.0 filed on Mar. 17, 2010, the contents of each of which are hereby incorporated by reference in their entireties.

BACKGROUND

Increased intraocular pressure is a frequent disorder of the eye which is often associated with optic nerve damage, in which case the disease is glaucoma. In the absence of optic nerve damage, the condition is referred to as ocular hypertension.

Normal intraocular pressure is usually defined as being in the range from 10 to 21 mmHg. The pressure results predominantly from balance between the production rate and the drainage rate of the aqueous humour in the eye. In addition, it is influenced by the corneal thickness and rigidity. The intraocular pressure typically fluctuates around about 15 to 16 mmHg with amplitudes of up to 6 mmHg. For example, it usually decreases in the night due to a decreased production of aqueous humour. It also responds to various physiological factors such as exercise, heart rate, respiration, fluid intake, as well as certain types of systemic or topical drugs.

The aqueous humour is produced by the ciliary bodies of the eye, from where it flows into the posterior chamber. The composition of the aqueous humour is very similar to that of blood plasma but differs from the latter by a lower protein content. Its main constituents are water (99%), electrolytes (inorganic ions to maintain the physiological pH), low amounts of albumin and β-globulins, ascorbate, glucose, lactate, and amino acids.

From the posterior chamber, the aqueous humour is distributed via the pupil of the iris into the anterior chamber of the eye. From here, it flows through the so-called trabecular meshwork, which is a spongy tissue area lined by trabeculocytes whose main function is to drain the humour into a set of tubes called Schlemm's canal, from where the humour enters the blood circulation. The humour flow from the trabecular meshwork into the Schlemm's canal occurs via two different routes: either directly via the aqueous vein to the episcleral vein, or indirectly via collector channels to the episcleral vein by intrascleral plexus. This trabecular outflow pathway accounts for the major fraction of drained aqueous humour. In addition, there exists a second major drainage pathway which is the uveoscleral outflow, which is relatively independent of the intraocular pressure and normally accounts for only 5 to 10% of the aqueous humour drainage in healthy humans.

Both in the trabecular meshwork and in the uveoscleral tissue, various prostanoid receptors have been found, which indicates that prostanoids are involved in the regulation of aqueous humour production and/or drainage and thereby influence the intraocular pressure. In the trabecular network, genes encoding the EP, FP, IP, DP and TP receptor families are expressed, whereas the EP and FP receptor families are dominant in the uveoscleral tissue (Toris et al., Surv Ophthalmol. 2008; 53, Suppl. 1, S107-S120).

Prostanoids are physiological fatty acid derivatives representing a subclass of eicosanoids. They comprise prostaglandins, prostamides, thromboxanes, and prostacyclins, all of which compounds are mediators involved in numerous physiological processes. Natural prostaglandins such as $PGF_{2\alpha}$, $PGE_2$, $PGD_2$, and $PGI_2$ exhibit a particular affinity to their respective receptors (FP, EP, DP, IP), but also have some non-selective affinity for other prostaglandin receptors (ibid.). Prostaglandins also have direct effects on matrix metalloproteinases. These are neutral proteinases expressed in the trabecular meshwork which play a role in controlling humour outflow resistance by degrading the extracellular matrix.

Several prostaglandin analogues have been found effective as topically administered medicines in reducing the intraocular pressure, such as latanoprost, bimatoprost, tafluprost, travoprost and unoprostone. By some experts, bimatoprost is understood as a prostamide rather than prostaglandin derivative.

Latanoprost, travoprost, tafluprost and probably also bimatoprost are potent and selective $PGF_{2\alpha}$ agonists. Their net effect is a reduction of intraocular pressure, which is predominantly caused by a substantial increase in aqueous humour drainage via the uveoscleral pathway. Probably they also increase the trabecular outflow to some degree.

Unoprostone is sometimes also classified as a $PGF_{2\alpha}$ analogue even though its potency and selectivity are much lower than in the case of the previously mentioned compounds. It is most closely related to a pulmonary metabolite of $PGF_{2\alpha}$. It is also capable of reducing the intraocular pressure, but appears to act predominantly by stimulating the trabecular drainage pathway, whereas it has little effect on the uveoscleral outflow.

Various eye drop formulations comprising prostaglandin analogues have been developed and are commercially available. Latanoprost and travoprost are provided as buffered, isotonised, preserved aqueous solutions in multidose bottles having a strength of 50 μg/mL (0.005%) and 40 μg/mL (0.004%), respectively. Tafluprost is available in a similar preserved formulations as well as in a non-preserved formulation in single-dose containers. The tafluprost formulations have a strength of 15 μg/mL (0.0015%) and additionally contain the surfactant, polysorbate 80. Bimatoprost is also marketed as a buffered, isotonised, and preserved aqueous solution; its strength is 0.3 mg/mL (0.03%). The strength of the commercial unoprostone formulation is 1.5 mg/mL (0.15%). It contains buffer, a preservative, an isotonising agent, and polysorbate 80.

However, preserved aqueous formulations for ophthalmic use are disadvantageous in that they are capable of producing irritancies or hypersensitivity reaction, in particular in long-term use, such as in glaucoma therapy. The most common preservative in the formulations mentioned above is benzalkonium chloride, a quaternary ammonium compound which is associated with frequent irritant toxic reactions. Non-preserved single use containers avoid this disadvantage, but they are expensive. Not only do they require a container for each single dose, but also an overfill of the formulation, which means that a substantial fraction (if not most) of the actual medicine remains in the container and is discharged as waste. Considering the drug in an eye drop which is actually administered into the eye, only a fraction of that becomes effective due to the limited volume capacity of the lacrimal sac: a significant fraction of the administered fluid volume is expelled by the blinking of the eyelids, and another fraction is taken up systemically via the nasolacrimal duct, which potentially leads to adverse drug effects.

In spite of the preservative contained in the currently available formulation of latanoprost, there have been reports of bacterial keratitis caused by microbiological contamination of the product assumingly by the patients themselves, indicating that the microbiological safety of the product is only relative.

An alternative to aqueous eye drop formulations are oil-based ophthalmic compositions. They are often capable of better dissolving poorly water-soluble drug substances. Moreover, they do not normally require the incorporation of pH adjusting agents or isotonising agents.

One of the disadvantages of all oil-based formulations for ophthalmic administration is that inherently have a negative impact on vision. Whether used as oily solutions or oil-in-water emulsions, they exhibit a refractive index which differs substantially from that of physiological tear fluid, which leads to visual disturbances and blurring.

Moreover, oil-based formulations do not readily mix with tear fluid to form a homogenous liquid phase. Oily solutions are altogether immiscible with the aqueous tear fluid, and the exact fate of an emulsion mixed with tear fluid in a physiological setting is not completely predictable.

Oil-in-water emulsions of poorly water-soluble drugs like ciclosporin further exhibit the disadvantage that they have a limited drug load capacity. While the active ingredient may have some solubility in the oil phase, this phase is only dispersed in the coherent aqueous phase of the emulsion so that the maximum overall drug concentration in the formulation is very limited.

In contrast to single phase systems such as aqueous or oily solutions, oil-in-water emulsions are also more complex and difficult to manufacture, especially in sterile form. Frequently, emulsions are not readily sterilisable by thermal treatment without negative impact on the physical properties of the emulsion. On the other hand, aseptic processing is complex, costly, and is associated with higher risks of failure, i.e. microbial contamination of the product.

Furthermore, oil-in-water emulsions are like aqueous solutions prone to microbial contamination during use. If they were to be presented in multi-dose containers which are in principle more cost-efficient and convenient for patients than single-use vials, they would have to be preserved in order to ensure their microbiological quality. At the same time, preservatives which can be used in ophthalmic formulations are potentially irritating, as mentioned above, or even damaging to the eye.

WO 2005/123035 discloses hydrophobic compositions which may be useful as ophthalmic drug formulations. The compositions may be used to treat various ophthalmic diseases and conditions including glaucoma and may comprise a therapeutic agent selected from various different therapeutic categories such as antibiotics, antimicrobials, antifungal agents, antiviral agents, antiparasitic agents, antiallergic agents, anti-inflammatory agents, alkylating agents, prostaglandin analogues and beta-blockers, cholinergic agents, vasoconstrictors, pupil size management agents, glaucoma agents, macular degeneration agents, and agents to arrest the development of cataracts. The hydrophobicity of the composition is achieved by selecting a hydrophobic liquid vehicle, selected in particular from silicon polymers, fluorinated silicon polymers, perfluorocarbons, fluorinated alcohols, and perfluorinated polyethers, and mixtures thereof. However, the only specific composition disclosed in the document does not incorporate an active ingredient, but is merely a vehicle consisting of a mixture of two silicon polymers, namely dimethicone and cyclomethicone, which have been combined so as to yield a viscosity of about 8,000 centistokes.

US 2002/128527 discloses semifluorinated alkanes and their preparation, and proposes their use as vehicles in ophthalmic preparations. However, it does not disclose any specific compositions comprising a semifluorinated alkane and an incorporated active ingredient. Neither does it mention the treatment of glaucoma or the incorporation of a prostaglandin analogue. It is also silent about ophthalmic vehicles comprising mixtures of semifluorinated alkanes and cosolvents.

U.S. Pat. No. 7,026,359 describes the use of highly fluorinated oligomeric alkanes in ophthalmology. These highly fluorinated compounds, whose chemical structure is different from that of the semifluorinated alkanes referred to in US 2002/128527, represent a large group of hydrocarbons having 2 to 6 perfluorinated side chains. The document does not mention any specific composition comprising such a fluorinated compound and an active ingredient. In fact, it does not make any reference to any particular active agent at all, or even to any specific chemically or functionally defined class of active ingredients. Neither does it disclose any specific therapeutic indications within ophthalmology in which the use of the highly fluorinated compounds could be useful.

U.S. Pat. No. 5,874,481 is directed to thermodynamically stable molecular solutions of lipophilic active ingredients in mixtures of a lipophilic fluorochemical and a non-fluorinated cosolvent. While the patent in a very general manner refers to numerous classes of therapeutic compounds from which the active ingredient may be selected, including ophthalmic agents, it only provides very few specific composition comprising a selected active ingredient, namely solutions of diazepam, caffeine and prednisone, respectively, all of which are systemic rather than ophthalmic therapeutic agents.

It is an object of the present invention to provide a novel pharmaceutical composition which is useful in the treatment of increased intraocular pressure, e.g. in association with open-angle glaucoma or ocular hypertension, which these issues discussed above and overcomes at least one of the limitations or disadvantages associated with prior art formulations. In a specific aspect, it is an object of the invention to provide an ophthalmic composition which has the capacity to incorporate substantial amounts of poorly water-soluble drug substances useful in the management of open-angle glaucoma and/or ocular hypertension. In a further aspect, it is an object of the invention to provide a pharmaceutical kit comprising a composition for the treatment of increased intraocular pressure which does not exhibit one or more of the disadvantages of prior art. Further objects of the invention will become clear on the basis of the following description, examples, and patent claims.

SUMMARY OF THE INVENTION

The present invention provides a pharmaceutical composition comprising a poorly water-soluble prostaglandin analogue useful in the management of increased intraocular pressure or a symptom associated therewith. The composition further comprises a liquid vehicle comprising a semifluorinated alkane.

In one of the preferred embodiments, the composition comprises a therapeutically effective amount of a poorly water-soluble prostaglandin analogue selected from the group consisting of latanoprost, bimatoprost, tafluprost, travoprost and unoprostone. It is furthermore preferred that the composition is in liquid form and adapted to be administered topically to the eye of a patient.

In a further aspect, the invention provides the use of such composition in the prevention or therapy of increased intraocular pressure, ocular hypertension, glaucoma, or any symptom associated therewith, wherein the prevention or treatment is preferably performed by administering the composition into the eye of a patient.

In yet a further aspect, the invention provides a pharmaceutical kit comprising such composition in a container which has a dispensing means adapted for topically administering the composition to the eye of a patient.

DETAILED DESCRIPTION OF THE INVENTION

In a first aspect, the invention provides a pharmaceutical composition comprising a therapeutically effective amount of a poorly water-soluble prostaglandin analogue useful in the prevention or therapy of increased intraocular pressure or a symptom associated therewith. The composition is further characterised in that it comprises a liquid vehicle comprising a semifluorinated alkane.

As used herein, a pharmaceutical composition is a composition comprising at least one pharmacologically active ingredient or diagnostic agent in combination with at least one pharmaceutical excipient. A therapeutically effective amount refers to a dose, concentration or strength which is useful for producing a desired pharmacological effect.

As described above, increased intraocular pressure may be associated with optic nerve damage, in which case the disease is glaucoma. In the absence of optic nerve damage, the condition is referred to as ocular hypertension. Increased intraocular pressure may be associated with a variety of conditions such as orbital oedema, traumatic hyphema, pupillary block, postoperative viscoelastic retention, intraocular inflammation, or corticosteroid use. Increased intraocular pressure is also a major risk factor for the development of glaucoma. Vice versa, glaucoma itself very often involves increased intraocular pressure. Further symptoms which may be directly or indirectly associated with increased intraocular pressure or with glaucoma in combination with increased intraocular pressure include optic neuropathy, disc haemorrhage, nerve fiber layer defects, notching, vertical ovalisation of the cup, asymmetric and/or progressive cupping, loss of visual field, halos, blurred vision, eye pain etc.

The active ingredient is selected from the group of poorly water-soluble prostaglandin analogues. Examples of such prostaglandin analogues include latanoprost, bimatoprost, tafluprost, travoprost and unoprostone. A particularly preferred active ingredient is latanoprost.

Some of the key advantages of the present invention are brought about by the presence of a semifluorinated alkane in the composition. Semifluorinated alkanes are linear or branched alkanes some of whose hydrogen atoms have been replaced by fluorine. In a preferred embodiment, the semifluorinated alkanes (SFA's) used in the present invention are composed of at least one non-fluorinated hydrocarbon segment and at least one perfluorinated hydrocarbon segment. Particularly useful are SFA's which have one non-fluorinated hydrocarbon segment attached to one perfluorinated hydrocarbon segment, according to the general formula $F(CF_2)_n(CH_2)_mH$, or two perfluorinated hydrocarbon segments separated by one non-fluorinated hydrocarbon segment, according to the general formula $F(CF_2)_n(CH_2)_m(CF_2)_oF$.

Another nomenclature which is used herein refers to the above-mentioned SFA's having two or three segments as RFRH and RFRHRF, respectively, wherein $R_F$ designates a perfluorated hydrocarbon segment, $R_H$ designates a non-fluorinated segment. Alternatively, the compounds may be referred to as FnHm and FnHmFo, respectively, wherein F means a perfluorated hydrocarbon segment, H means a non-fluorinated segment, and n, m and o is the number of carbon atoms of the respective segment. For example, F3H3 is used for perfluoropropylpropane. Moreover, this type of nomenclature is usually used for compounds having linear segments. Therefore, unless otherwise indicated, it should be assumed that F3H3 means 1-perfluoropropylpropane, rather than 2-perfluoropropylpropane, 1-perfluoroisopropylpropane or 2-perfluoroisopropylpropane.

Preferably, the semifluorinated alkanes according to the general formulas $F(CF_2)_n(CH_2)_mH$ and $F(CF_2)_n(CH_2)_m(CF_2)_oF$ have segment sizes ranging from 3 to 20 carbon atoms, i.e. n, m and o are independently selected in the range from 3 to 20. SFA's which are useful in the context of the present invention are also described in EP-A 965 334, EP-A 965329 and EP-A 2110126, the disclosure of which documents is incorporated herein.

In a further embodiment, the semifluorinated alkane is a compound according to the formula RFRH, whose segments $R_F$ and $R_H$ are linear and each—but independently from one another—have from 3 to 20 carbon atoms. In another particular embodiment, the perfluorinated segment is linear and comprises from 4 to 12 carbon atoms, and/or the non-fluorinated segment is linear and comprises from 4 to 8 carbon atoms. Preferred SFA's include in particular the compounds F4H5, F4H6, F6H4, F6H6, F6H8, and F6H10. Presently most preferred for carrying out the invention are F4H5, F4H6, F6H6 and F6H8.

Optionally, the composition may comprise more than one SFA. It may be useful to combine SFA's, for example, in order to achieve a particular target property such as a certain density or viscosity. If a mixture of SFA's is used, it is furthermore preferred that the mixture comprises at least one of F4H5, F4H6, F6H4, F6H6, F6H8, and F6H10, and in particular one of F4H5, F6H6 and F6H8. In another embodiment, the mixture comprises at least two members selected from F4H5, F4H6, F6H4, F6H6, F6H8, and F6H10, and in particular at least two members selected from F4H5, F6H6 and F6H8.

Liquid SFA's are chemically and physiologically inert, colourless and stable. Their typical densities range from 1.1 to 1.7 g/cm$^3$, and their surface tension may be as low as 19 mN/m. SFA's of the RFRH type are insoluble in water but also somewhat amphiphilic, with increasing lipophilicity correlating with an increasing size of the non-fluorinated segment.

Liquid SFA's of the RFRH type are being used commercially for unfolding and reapplying a retina, for long-term tamponade as vitreous humour substitute (H. Meinert et al., European Journal of Ophthalmology, Vol. 10(3), pp. 189-197, 2000), and as wash-out solutions for residual silicon oil after vitreo-retinal surgery. Experimentally, they have also been used as blood substitutes (H. Meinert et al., Biomaterials, Artificial Cells, and Immobilization Biotechnology, Vol. 21(5), pp. 583-95, 1993). These applications have established SFA's as physiologically well tolerated compounds.

On the other hand, SFA's have not been used as excipients in approved drug products as of today.

It has now surprisingly been found by the inventors that SFA's are particularly suitable as carriers, vehicles or excipients in ophthalmic compositions for topical administration. This is based on the fact that SFA's are capable of dissolving many poorly water-soluble compounds which are of interest in ophthalmology, but also on the discovery that they are unexpectedly well-tolerated by the eye, as shown in preclinical testing. This is very surprising as organic or non-aqueous solvents, perhaps with the exception of oily compounds, are typically very irritating or even highly damaging when administered topically to an eye.

Compared to oily carriers or vehicles in ophthalmic compositions for topical use, SFA's exhibit a refractive index which is much better compatible with the aim of a minimally affected vision: While oily preparation lead to a blurry vision and can therefore not be administered in any situation in which the patient needs a clear vision, SFA's cause little or no blurring.

By illustration, the refractive index of tear fluid is close to that of water, i.e. 1.333 at room temperature (RT). Oils typically have a substantially higher refractive index such as about 1.46 (peanut oil), 1.47 (sesame oil), or 1.48 (castor oil). In contrast, the inventors have determined the refractive indices of various SFA's of interest to be in the region of 1.29 to 1.35, i.e. much closer to that of water. In one of the specific embodiments, the invention is therefore practised with an SFA whose refractive index is from 1.29 to 1.35, and in particular from about 1.30 to about 1.35 at 20° C. The refractive index for selected SFA's is shown in table 1.

Moreover, SFA's exhibit a remarkable wetting and spreading behaviour by which they deliver an incorporated active ingredient rapidly and effectively to the corneal surface and conjunctiva. Wetting means the ability of a liquid to establish and maintain contact with a solid surface, resulting from intermolecular interactions when the two are brought together. The balance between adhesive and cohesive forces determines the degree of wetting. The higher the adhesive forces compared to the cohesive forces, the more a drop of liquid will spread across the surface of the solid material. Conversely, very high cohesive forces within the liquid will cause the drop to form a sphere, thus avoiding contact with the surface. Similarly, spreading may also occur at the interface of two liquids which are brought into contact with each other.

TABLE 1

| SFA | Refractive index |
|---|---|
| F4H4 | 1.308 |
| F4H5 | 1.3204 |
| F4H6 | 1.334 |
| F4H7 | 1.3357 |
| F4H8 | 1.348 |
| F6H2 | 1.295 |
| F6H4 | 1.306 |
| F6H6 | 1.3224 |
| F6H7 | 1.3366 |
| F6H8 | 1.3432 |
| F6H9 | 1.3494 |

A measure for wetting and spreading is the contact angle θ. The contact angle is the angle at which the liquid-vapour interface meets the solid-liquid or liquid-liquid interface. The tendency of a drop to spread out increases as the contact angle decreases. Thus, the contact angle provides an inverse measure of wettability.

A low contact angle of less than 90° indicates high wettability and/or spreading, whereas a higher contact angle indicates poor wettability and spreading. Perfect wetting and spreading results in a contact angle of 0°, also reported as no measurable contact angle.

The inventors have found that the SFA's used in the present invention, in particular the preferred SFA's, exhibit an excellent wetting of various surfaces which are not easily wetted by conventional drug formulations. For example, the contact angle of both F4H5 and F6H8 on tablets compressed from either trospium chloride or fenofibrate (150 mg of drug substance compressed at 15-20 kN to tablets of 13 mm in diameter) was not measurable, i.e. perfect wetting occurred. It is noted that fenofibrate is an example of a hydrophobic, poorly water-soluble compound, whereas trospium chloride is hydrophilic and water-soluble. In comparison, the contact angle of purified water on the fenofibrate tablet was determined as 92.5°, i.e. the tablet was poorly wetted by water.

A further surprising advantage of SFA's found by the inventors is that they appear to form very small droplets when dispensed from a dropper such as an eye dropper. Without wishing to be bound by theory, it is believed that the small droplet size is a result of an interplay of the SFA's unique properties in terms of their density, viscosity, and surface tension. In any case, it is believed that for topical administration into an eye a small drop or volume of administration is highly advantageous as the capability of the lacrimal sac to accept and hold fluid is extremely limited. In fact, it is very common that the administration of a conventional eye drop formulation based on water or oil immediately leads to a discharge of a substantial fraction of the administered medicine as well as some tear fluid. At the same time, there is a risk that some of the administered dose will be taken up systemically via the nasolacrimal duct. Hence, if an effective dose of an active ingredient can be incorporated in a small volume of liquid which can be dispensed as a very small droplet, this should lead to a substantially increased dosing reliability and reproducibility, thus enhancing the safety and effectiveness of the therapy.

A yet further advantage of the invention which is based on the use of SFA's is that they can be designed or mixed for an optimally adjusted evaporation behaviour after administration. Thus it is possible to formulate an ophthalmic composition which delivers an active compound efficiently to the eye in such a way that the liquid vehicles is subsequently eliminated via evaporation. This is in sharp contrast to oily eye drop vehicles which do not evaporate and thus form non-physiological residues at the site of administration, e.g. in the lacrimal sac.

Moreover, the invention provides a means of formulating non-aqueous ophthalmic compositions which are microbiologically stable. This is due to the fact that SFA's are not normally prone to microbial contamination. Hence, it is possible to formulate preservative-free ophthalmic compositions which are better tolerable for many patients, in particular patients suffering from ophthalmic disorders.

As mentioned, the active ingredient to be selected for carrying out the invention is a compound useful in the management, prevention or therapy of increased intraocular pressure, or of any symptom associated with this condition, and selected from the group of poorly water-soluble prostaglandin analogues.

It is believed that the invention is particularly useful if the active compound is selected from poorly water-soluble drug substances which are otherwise challenging to formulate for ophthalmic use. As used herein, a compound is poorly water-soluble if it exhibits a solubility falling into the definitions of "sparingly soluble", "slightly soluble", "very slightly soluble", or "practically insoluble" (according to Ph. Eur. 6th Ed.). Particularly preferred are active ingredients which are "very slightly soluble" or "practically insoluble". In another embodiment, it is preferred that the active ingredient exhibits a water solubility of less than about 1 mg per mL, as measured at room temperature (between 15 and 25° C.) and at neutral pH (pH 6.0 and pH 8.0).

Examples of preferred active compounds include latanoprost, bimatoprost, tafluprost, travoprost and unoprostone. Latanoprost, also known as isopropyl-(Z)-7[(1R,2R,3R,5S) 3,5-dihydroxy-2-[(3R)-3-hydroxy-5-phenylpentyl]cyclopentyl]-5-heptenoate, like travoprost and unoprostone, is a colourless to slightly yellow oil and practically insoluble in water. The IUPAC name of travoprost is propan-2-yl 7-[3, 5-dihydroxy-2-[3-hydroxy-4-[3-(trifluoromethyl)phenoxy]-but-1-enyl]-cyclopentyl]hept-5-enoate. Unoprostone is currently used as unoprostone isopropyl, also known as isopropyl (+)-(Z)-7-[(1R,2R,3R,5S)-3,5-dihydroxy-2-(3-oxodecyl)cyclopentyl]-5-heptenoate. Bimatoprost may also be referred to as 7-[3,5-dihydroxy-2-(3-hydroxy-5-phenyl-pent-1-enyl)-cyclopentyl]-N-ethyl-hept-5-enamide. Bimatoprost, or (Z)-7-[(1R,2R,3R,5S)-3,5-Dihydroxy-2-[(1E,3S)-3-hydroxy-5-phenyl-1-pentenyl]cyclopentyl]-N-ethyl-5-heptenamide, is a powder and slightly soluble in water. The chemical name of tafluprost is isopropyl (5Z)-7-{(1R,2R, 3R,5S)-2-[(1E)-3,3-difluoro-4-phenoxybut-1-en-1-yl]-3,5-dihydroxycyclopentyl}hept-5-enoate.

A particularly preferred active compound according to the present invention is latanoprost. Latanoprost may be incorporated in a composition of the invention at any therapeutically useful concentration, such as from about 1 µg/ml to about 1 mg/ml. In further embodiments, the concentration of latanoprost is from about 10 µg/ml to about 500 µg/ml, or at least about 20 µg/ml, or from about 20 µg/ml to about 100 µg/ml. In the case of other active ingredients, the preferred concentrations may be different. For example, unoprostone or unoprostone isopropyl may be incorporated at a concentration of about 0.1 mg/ml to about 10 mg/ml, or from about 0.5 mg/ml to about 5 mg/ml, respectively.

It is also preferred that the active ingredient is incorporated in the dissolved state. This allows the composition to be formulated as a clear solution. Alternatively, the composition may also be designed as a suspension or emulsion.

It has been found by the inventors that certain SFA's have a surprisingly high capacity to dissolve even extremely challenging poorly soluble compounds. In some of the preferred embodiments, ophthalmic solutions comprise an SFA selected from F4H5, F4H6, F6H6, and F6H8 and latanoprost as active ingredient. Within these embodiments, it is preferred that the concentration of latanoprost is about 0.001 wt.-% to about 0.01 wt.-%.

Depending on the active ingredient, its dose and the SFA or mixture of SFA's selected as carrier, it may be useful to add another liquid excipient in order to ensure that the active compound can be incorporated in completely dissolved form. Such other liquid excipient is preferably an organic cosolvent, such as an oil selected from glyceride oils, liquid waxes, and liquid paraffin, or an organic solvent exhibiting a high degree of biocompatibility.

Examples of potentially useful oily excipients which may be used in combination with one or more SFA's include triglyceride oils (i.e. soybean oil, olive oil, sesame oil, cotton seed oil, castor oil, sweet almond oil), mineral oil (i.e. petrolatum and liquid paraffin), medium chain triglycerides (MCT), oily fatty acids, isopropyl myristate, oily fatty alcohols, esters of sorbitol and fatty acids, oily sucrose esters, or any other oily substance which is physiologically tolerated by the eye. In one of the preferred embodiments, the concentration of the oily excipient is up to about 30 wt.-%, such as in the range from about 0.1 to 20 wt.-%.

Examples of potentially useful organic solvents include glycerol, propylene glycol, polyethylene glycol, and ethanol. However, the concentration of the cosolvent should preferably be low relative to that of the SFA or SFA mixture. If an organic solvent such as ethanol is used, it is recommendable to keep it below a level of approx 5 wt.-%. More preferably, the content of ethanol is from about 0.1 to about 2 wt.-%, and most preferably not more than about 1.5 wt.-%.

While ethanol, generally speaking, is not very well tolerated by the human eye, it has surprisingly been found by the inventors that mixtures of semifluorinated alkanes with very small amounts of ethanol, such as 1 wt.-%, are capable of dissolving substantially higher amounts of a hydrophobic, poorly soluble compound such as latanoprost, whereas the tolerability of the composition is not negatively affected by the ethanol content.

The composition may of course comprise further pharmaceutical excipients as required or useful. Potentially useful excipients include surfactants, in particular non-ionic surfactants or amphiphilic lipids, acids, bases, antioxidants, stabilisers, synergists, and—if required in a particular case—a preservative.

Surfactants which are considered potentially useful include tyloxapol, poloxamers such as Pluronic F68LF or Lutrol F68, Pluronic L-G2LF and Pluronic L62D, polysorbates such as polysorbate 20 and polysorbate 80, polyoxyethylene castor oil derivatives, sorbitan esters, polyoxyl stearates, and mixtures of two or more thereof.

Furthermore, the invention provides a pharmaceutical kit comprising the composition as described above and a container holding the composition. Preferably, the container which contains the composition has a dispensing means such as a dropping device adapted for topically administering the composition to the eye of a patient.

The following examples serve to illustrate the invention; however, these are not to be understood as restricting the scope of the invention.

EXAMPLES

Example 1

The droplet size of selected SFA's in terms of weight and volume of droplets from three droppers was determined and compared to that of purified water. The devices used for dispensing the droplets were (a) a 2 mL Pasteur pipette (wall thickness 0.53 mm; external tip diameter: 1.50 mm; length: 150 mm) made of glass, (b) a 20 G (0.9 mm×50 mm) injection needle, and (c) a dropper from a commercial eye drops product (Hylo-Vision). The droplet weights were measured at 25° C. using a laboratory balance; the volumes were calculated. Each test was performed 10 times. The results of the experiments (mean values of droplet sizes and standard deviations) are shown in table 2.

TABLE 2

| | Glass pipette | | Injection needle | | Eye dropper | |
|---|---|---|---|---|---|---|
| Material | mg | µL | mg | µL | mg | µL |
| Water | 31.2 ± 1.4 | 31.3 ± 1.4 | 11.0 ± 0.9 | 11.1 ± 0.9 | 36.0 ± 2.2 | 36.1 ± 2.2 |

TABLE 2-continued

|  | Glass pipette | | Injection needle | | Eye dropper | |
|---|---|---|---|---|---|---|
| Material | mg | μL | mg | μL | mg | μL |
| F4H5 | 6.0 ± 0.4 | 4.7 ± 0.3 | 2.6 ± 0.4 | 2.0 ± 0.3 | 12.4 ± 0.2 | 9.6 ± 0.2 |
| F6H8 | 6.6 ± 0.6 | 5.0 ± 0.4 | 3.4 ± 0.2 | 2.5 ± 0.1 | 13.7 ± 0.4 | 10.3 ± 0.3 |

Table 2 shows that droplets of F4H5 and F6H8 are dramatically smaller and lighter than water droplets dispensed from the same device. Taking into account the fact that SFA's have a high capacity to dissolve many active ingredients very well, it is concluded that SFA's are highly suitable liquid vehicles for eye drops which are better retained by the lacrimal sac, produce little spill-over, and thus have a potential to deliver a dose more reliably and reproducibly to the eye than conventional eye drop formulations.

Example 2

Ethanol was mixed with F4H5 to yield a solution having an ethanol concentration of 1 wt.-%. The solution was filtered aseptically and filled into sterile vials. The physiological tolerability of this solution was evaluated in an ex-vivo eye irritation test (EVEIT) using rabbit eyes taken from freshly sacrificed animals. The eyes were fastened in chambers coupled micropump systems which continuously supplied the eyes with cultivation medium (Minimal Essential Medium, MEM T031-05) without fetal calf serum. The vitality of the eyes was monitored by regularly measuring the concentration of lactate and glucose in the chamber eluate. The corneal surface of the eyes was damaged by abrasion, using a dental ceramic abrasive (638XF, Meisinger). For each eye, four lesions of 3.0 to 4.5 mm$^2$ were prepared.

To evaluate the effect of F4H5 and F4H5 with 1 wt.-% ethanol on the cornea, an amount of approx. 0.25 to 0.50 μl of the respective test substance was dropped onto the centre of a cornea once every hour over a period of 12 hours, followed by a 12 hour resting period in which the cornea was submersed in culture medium to simulate a closed lid during a night phase. In addition, an aqueous solution of hyaluronic acid (0.1 wt.-%) was used as reference (hyaluronic acid is know to enhance the restoration of the corneal surface after damage), culture medium was used as control, and aqueous benzalkonium chloride solution (0.01 wt.-%) was used as negative control. Each test was performed over a period of 3 days. The effects were observed by optical coherence tomography (OCT), by digitally determining the dimensions of the lesions after staining with fluorescein, and finally by a histological evaluation of the corneal epithelium and endothelium at the end of each experiment.

In result, it was found that in particular F4H5 was better tolerated than culture medium, and that it exhibits a positive effect on the healing of damaged cornea similar to that of hyaluronic acid. Even when comprising 1 wt.-% of ethanol, F4H5 is tolerated very well by the eye. OCT imaging revealed no indication of penetration of F4H5 into the cornea.

In more detail, it was found that the lesions prepared by abrasion became smaller or larger over time depending on the liquid that was administered to the cornea. Substantial healing occurred when F4H5, F4H5 with 1 wt.-% ethanol, or hyaluronic acid was used. In marked contrast, benzalkonium chloride administration lead to a rapid growth of the lesions eventually leading to a complete disintegration of the corneal epithelium. Culture medium had an intermediate effect. Tables 3 and 4 shows the dimensions of the lesions [mm$^2$] before and after the tests with the various test liquids and controls, respectively.

Morphological and histological evaluation revealed that the corneas treated with F4H5 or hyaluronic acid had not only healed very well, but were also entirely clear at the end of the tests, with healthy and smooth surface morphology. Eyes treated with F4H5 with 1 wt.-% ethanol showed a healthy overall morphology, the corneas were clear and the epithelia revealed only very minor signs of damage remaining from the lesions. In contrast, some of the controls treated with culture medium showed significant surface roughness, and the eye treated with benzalkonium chloride showed not only the complete disintegration of the corneal epithelium, but also a major impairment of the complete cornea even including the endothelium.

TABLE 3

|  | F4H5 | | | F4H5 + 1% EtOH | |
|---|---|---|---|---|---|
|  | Run 1 | Run 2 | Run 3 | Run 1 | Run 2 |
| Initial size [mm$^2$] | 9.95 | 12.88 | 12.09 | 14.68 | 14.99 |
| Final size [mm$^2$] | 0.19 | 1.01 | 0.06 | 0.30 | 2.26 |
| Change [%] | −98.1 | −99.0 | −99.5 | −98.0 | −84.9 |

*EtOH: ethanol

TABLE 4

|  | HA | | | MEM | | | |
|---|---|---|---|---|---|---|---|
|  | Run 1 | Run 2 | Run 3 | Run 1 | Run 2 | Run 3 | BAC |
| Initial size [mm$^2$] | 13.22 | 16.03 | 14.87 | 15.5 | 15.57 | 13.11 | 16.05 |
| Final size [mm$^2$] | 0.36 | 0.24 | 0.00 | 2.51 | 6.83 | 0.00 | >60 |
| Change [%] | −97.3 | −98.5 | −100 | −83.8 | −56.1 | −100 | ** |

*HA: hyaluronic acid; BAC: benzalkonium chloride; MEM: minimal essential medium
**Lesion essentially covered the complete corneal surface Example 3

The ex-vivo eye irritation test (EVEIT) according to example 2 was repeated, this time using F6H8 and F6H8 mixed with 1 wt.-% ethanol as vehicles whose tolerability was to be evaluated. Each of the two vehicles was tested in two separate runs. In result, all lesions healed fully during the experimental time (see table 5). Histology showed dense stromata with very few clefts and well-arranged keratocytes.

TABLE 5

|  | F6H8 | | F6H8 + 1% EtOH | |
|---|---|---|---|---|
|  | Run 1 | Run 2 | Run 1 | Run 2 |
| Initial size [mm$^2$] | 10.54 | 12.08 | 16.65 | 11.29 |
| Final size [mm$^2$] | 0.00 | 0.00 | 0.00 | 0.00 |
| Change [%] | −100.0 | −100.0 | −100.0 | −100.0 |

Example 4

0.25 mg of latanoprost were dissolved in 5 ml of a solution of ethanol (1 wt.-%) in F4H5. The resulting clear solution having a latanoprost concentration of 0.05 mg/ml (0.005% w/v) was aseptically filtered and filled into sterile vials. The refractive index at 20° C. was 1.322.

In a separate experiment, the solubility of latanoprost in a mixture of F4H5 and ethanol (ratio 99:1 by weight) was determined by HPLC according to Ph.Eur.2.2.29 after rotation evaporation of the solvent methyl acetate in vacuo, addition of the solvent under examination of the residue and determination of the dissolved amount. The solubility was found to be 0.057 mg/mL.

Example 5

1.5 mg of bimatoprost were dissolved in 5 ml of a solution of ethanol (1 wt.-%) in a mixture of F4H5 and F6H8 (1:1). The resulting clear solution having a bimatoprost concentration of 0.3 mg/ml (0.03% w/v) was aseptically filtered and filled into sterile vials. The refractive index at 20° C. was 1.333.

Example 6

0.075 mg of tafluprost and 20 mg of alpha-tocopherol were dissolved in 5 ml of a solution of ethanol (1 wt.-%) and medium-chain triglycerides (10 wt.-%) in F6H8. The resulting clear solution having a tafluprost concentration of 0.015 mg/ml (0.0015% w/v) and an alpha-tocopherol concentration of 4 mg/ml was aseptically filtered and filled into sterile vials. The refractive index at 20° C. was 1.359.

Example 7

0.2 mg of travoprost were dissolved in 5 ml of a solution of ethanol (1 wt.-%) in F6H6. The resulting clear solution having travoprost a concentration of 0.04 mg/ml (0.004% w/v) was aseptically filtered and filled into sterile vials. The refractive index at 20° C. was 1.331.

Example 8

7.5 mg of unoprostone were dissolved in 5 ml of a solution of ethanol (1 wt.-%) in F4H6. The resulting clear solution having a unoprostone concentration of 1.5 mg/ml (0.15% w/v) was aseptically filtered and filled into sterile vials. The refractive index at 20° C. was 1.334.

Example 9

0.5 mg of latanoprost were dissolved in 5 ml of a solution of ethanol (0.75 wt.-%) in a mixture of F4H5 and F4H6 (1:2). The resulting clear solution having a latanoprost concentration of 0.1 mg/ml (0.01% w/v) was aseptically filtered and filled into sterile vials. The refractive index at 20° C. was 1.336.

Example 10

0.25 mg of latanoprost were dissolved in 5 ml of a solution of ethanol (0.5 wt.-%) and olive oil (4 mg/ml) in F4H5. The resulting clear solution having a latanoprost concentration of 0.05 mg/ml (0.005% w/v) was aseptically filtered and filled into sterile vials. The refractive index at 20° C. was 1.322.

Example 11

0.25 mg of latanoprost were dissolved in 5 ml of a solution of ethanol (0.25 wt.-%) in F4H6. The resulting clear solution having a latanoprost concentration of 0.05 mg/ml (0.005% w/v) was aseptically filtered and filled into sterile vials. The refractive index at 20° C. was 1.334.

Example 12

An antimicrobial preservative effectiveness test in analogy to that of USP 32 <51> was carried out. Sample vials comprising F4H5 or F6H8, respectively, were inoculated with *Escherichia coli, Pseudomonas aeruginosa, Staphylococcus aureus, Candida albicans* and *Aspergillus niger* and incubated at approx. 22.5° C. The results are given in tables 6 and 7.

In result, no increase but a substantial decrease in the concentration of colony-forming units (cfu) over 24 and 48 hours was observed. Obviously, the compounds do not support microbial growth, but rather inhibit it in the same manner as if an effective amount of an antimicrobial preservative had been added.

TABLE 6

| F6H8 (pure) Organism | cfu/mL | | | | Change in log steps | | |
|---|---|---|---|---|---|---|---|
|  | 0 h | 24 h | 48 h | 6 d | 24 h | 48 h | 6 d |
| *E. coli* (ATCC 8739) | 1 600 | <100 | <100 | n.d. | ≤−1.2 | ≤−1.2 | n.d. |
| *P. aeruginosa* (ATCC 9027) | 1 600 | <100 | <100 | n.d. | ≤−1.2 | ≤−1.2 | n.d. |
| *S. aureus* (ATCC 6538) | 2 900 | <100 | <100 | n.d. | ≤−1.4 | ≤−1.4 | n.d. |
| *C. albicans* (ATCC 10231) | 1 500 | <100 | <100 | n.d. | ≤−1.2 | ≤−1.1 | n.d. |
| *A. niger* (ATCC 16404) | 1 500 | <100 | <100 | <100 | ≤−1.2 | ≤−1.2 | ≤−1.2 |

TABLE 7

| F4H5 (pure) | cfu/mL | | | | Change in log steps | | |
|---|---|---|---|---|---|---|---|
| Organism | 0 h | 24 h | 48 h | 6 d | 24 h | 48 h | 6 d |
| E. coli (ATCC 8739) | 1 600 | <100 | <100 | n.d. | ≤−1.2 | ≤−1.2 | n.d. |
| P. aeruginosa (ATCC 9027) | 1 600 | <100 | <100 | n.d. | ≤−1.2 | ≤−1.2 | n.d. |
| S. aureus (ATCC 6538) | 2 900 | <100 | <100 | n.d. | ≤−1.4 | ≤−1.4 | n.d. |
| C. albicans (ATCC 10231) | 1 500 | <100 | <100 | n.d. | ≤−1.2 | ≤−1.1 | n.d. |
| A. niger (ATCC 16404) | 3 000 | <100 | <100 | <100 | ≤−1.4 | ≤−1.2 | ≤−1.2 |

The invention claimed is:

1. A method for the treatment or prophylaxis of a disease or disorder selected from increased intraocular pressure, ocular hypertension, glaucoma, or a symptom associated therewith, comprising the step of administering to a patient in need thereof, a pharmaceutical composition comprising:
   (a) a therapeutically effective amount of a poorly water-soluble prostaglandin analogue selected from the group consisting of latanoprost, bimatoprost, tafluprost, travoprost and unoprostone, and
   (b) a liquid vehicle comprising a semifluorinated alkane selected from F4H5, F4H6, F6H6 and F6H8;
wherein the composition is substantially free of water and free of a preservative and is adapted for topical administration to the conjunctiva or the corneal surface of an eye of a patient; and
wherein the composition is formulated as a solution, emulsion or suspension.

2. The method of claim 1, wherein the active ingredient is latanoprost.

3. The method of claim 2, wherein the concentration of latanoprost is from about 0.001 wt.-% to about 0.01 wt.-%.

4. The method of claim 1, wherein the composition is formulated as a solution.

5. The method of claim 1, further comprising an organic cosolvent.

6. The method of claim 5, comprising ethanol at a concentration of about 1.5 wt.-% or less, or of about 1.0 wt.-% or less.

7. The method of claim 2, wherein the semifluorinated alkane is F4H5, being formulated as a solution.

8. The method of claim 7, further comprising an organic co-solvent.

9. The method of claim 8, wherein the organic co-solvent is ethanol at a concentration of about 1.5 wt.-% or less.

10. The method of claim 9, wherein the concentration of latanoprost is from about 0.001 wt.-% to about 0.01 wt.-%.

* * * * *